United States Patent [19]

Metzger

[11] Patent Number: 5,050,297

[45] Date of Patent: Sep. 24, 1991

[54] METHOD FOR ASSEMBLY OF A DIRECTLY EXPOSED CATHETER SENSOR ON A SUPPORT TIP

[75] Inventor: Mark G. Metzger, San Jose, Calif.

[73] Assignee: Becton, Dickinson and Company, Franklin Lakes, N.J.

[21] Appl. No.: 410,564

[22] Filed: Sep. 21, 1989

[51] Int. Cl.⁵ .......................................... H01R 43/00
[52] U.S. Cl. ....................................... 29/855; 29/825; 73/716; 128/675
[58] Field of Search ................... 73/716; 29/825, 855; 128/675

[56] References Cited

U.S. PATENT DOCUMENTS

| | | | |
|---|---|---|---|
| 3,710,781 | 1/1973 | Hutchins, IV et al. | 128/675 |
| 3,748,623 | 7/1973 | Millar | 73/782 X |
| 4,274,423 | 6/1981 | Mizuno et al. | 128/675 |
| 4,722,348 | 2/1988 | Ligtenberg et al. | 128/675 |
| 4,730,389 | 3/1988 | Baudino et al. | 29/825 |
| 4,809,704 | 3/1989 | Sogawa et al. | 128/675 |
| 4,815,471 | 3/1989 | Stobie | 128/675 |

Primary Examiner—Carl J. Arbes
Attorney, Agent, or Firm—Aaron Passman

[57] ABSTRACT

A catheter sensor assembly and support has a member with a distal end and a proximal extension joined by an intermediate part. An open passage extends along the proximal extension and across the intermediate part to carry a sensor overlaying the passage. Conductors attach to the sensor bottom for transmitting signals from the sensor through a catheter lumen. An adhesive sealant secures the sensor to the intermediate part near the distal end so that the passage remains open between the lumen and the bottom. A method for assembling and supporting a sensor at a distal end of a catheter tube includes steps of attaching a sensor with an area toward an end connected to electrical conductors, placing a tube in the passage to provide a passageway between the lumen and the sensor, mounting the sensor to the member overlying the passage, inserting the proximal extension into the lumen with the electrical conductors passing through the lumen and sealing the sensor to the passage.

5 Claims, 3 Drawing Sheets

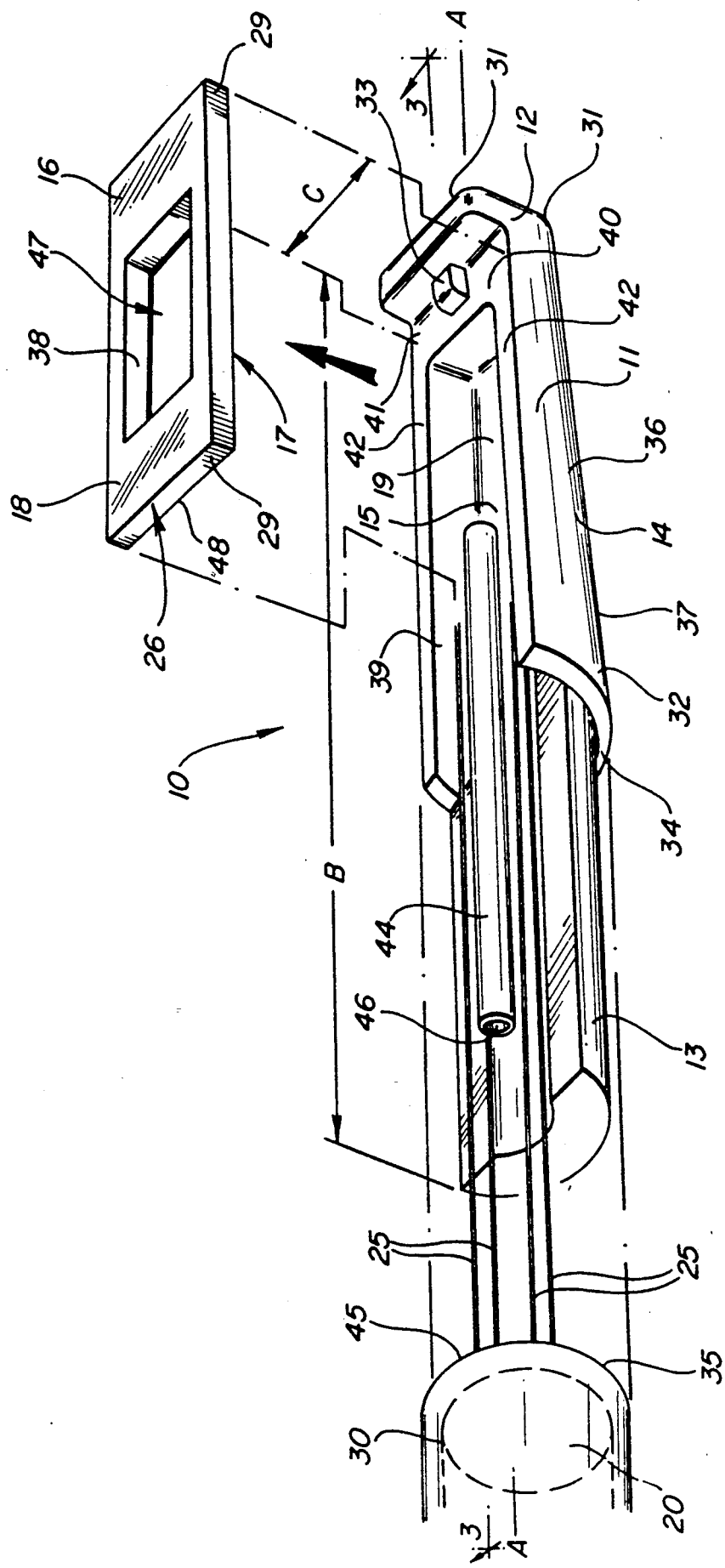

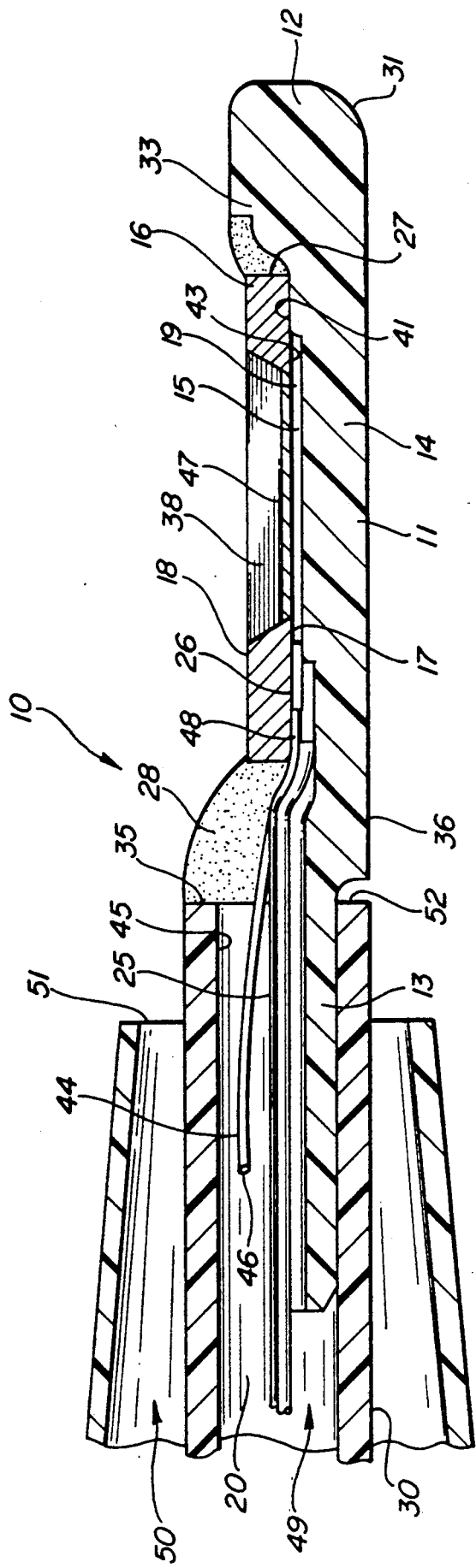

METHOD FOR ASSEMBLY OF A DIRECTLY EXPOSED CATHETER SENSOR ON A SUPPORT TIP

BACKGROUND OF THE INVENTION

1. Field of the Invention

This invention relates to a catheter or probe with a sensor for placement within a human or animal to allow direct monitoring within the body, and more particularly, relates to a support between the sensor and an end of the catheter and a method of assembling the sensor to the support and the catheter or probe.

2. Background Art

Catheters have been inserted into humans and animals for diagnosis, monitoring and treatment purposes and such catheters have to be small and flexible in size and structure in order to function without irritating the body part into which they are placed. Typically, catheters are used to infuse medications or remove samples for purposes of analysis. Multilumen catheters are sometimes used to infuse medication and remove samples at the same time.

If a sample is removed for purposes of analysis, it has to be taken to a laboratory, analysis made and the results transmitted to the doctor. Delay in performing the analysis and transmitting the data sometimes can be fatal to the patient. Another use of a catheter is to form a hydraulic column for transmitting pressure readings to an external sensor. In connection with pressure sensors, the hydraulic column has problems of air bubbles, kinks in the tubing of the column and blood clots each of which tends to affect the reliability, waveform fidelity and the accuracy and precision of the readings.

Ideally, the catheter should be about 20 gauge in size to provide an instrument for therapy or diagnosis which is easily inserted and easy to use without irritation or injury to the body. Twenty gauge catheters are commonly used on all but pediatric patients without problems of introduction or irritation when using such catheters, particularly, in connection with peripheral vessels. A pressure sensor on the distal tip of a 20 gauge catheter or probe would eliminate the mentioned hydraulic column difficulties.

Catheter tip pressure sensors have heretofore been relatively large in size, complicated in design, and costly to manufacture and use; therefore, such catheters have not been disposable. For preventing spread of disease and infection an inexpensive and reliable single use catheter tip pressure sensor is desired. The design for a sensor support and the method of using that support to aid in assembly is also needed.

Catheters having sensors are known and include sensors mounted at the distal tip of the catheter. U.S. Pat. No. 3,710,781 shows a catheter tip pressure sensor wherein a pair of elongate pressure sensor elements are mounted on opposite sides of a support. This is done to permit as large a sensor area as practical for purposes of providing accurate reproductions of blood pressure wave forms. U.S. Pat. No. 3,480,083 shows an apparatus for measuring esophageal motility, i.e., the squeezing pressure of the esophagus. The catheter in this patent has pressure sensitive sensors spaced lengthwise along and resiliently mounted on the catheter tube for measuring variations in pressure while in or passing through the esophagus. The sensors are formed of miniaturized discrete electronic components connected to a pressure responsive diaphragm and are supported within the tube by cylindrical holders fit within the tube for holding the diaphragm at the exterior surface on the side of the tube.

U.S. Pat. No. 3,545,275 shows a device responsive to impedance used for measuring pressure with a miniaturized sensor. The sensor is responsive to diaphragm fluctuations where the diaphragm is mounted in the distal end of a small diameter tube. A small probe is disclosed in U.S. Pat. No. 3,811,427 wherein a pair of electrodes are mounted in a liquid filled chamber and are sensitive to fluctuations in a diaphragm mounted at the distal end of a catheter tube. The probe is said to be smaller than one millimeter. Two embodiments are shown. Each has a diaphragm in the distal end of the catheter and a longitudinal separator which carries the pressure responsive means and isolates the liquid from the remainder of the catheter such that fluctuations in the diaphragm are transmitted to the separator which is generally longitudinally disposed.

U.S. Pat. No. 3,748,623 discloses a sensor support which is held to the catheter tube by an outer sleeve extending distally from the end of the catheter. A shelf-like member designed to flex in response to pressure loads is the distal part of the upper portion of the sleeve. Beneath this shelf is mounted the pressure sensor. U.S. Pat. No. 4,274,423 discloses a pressure sensor mounted in the end of a needle tube exposed to a pressure-receiving hole on the side of the needle tube a pre-determined distance from the end of the needle. A support member is provided with a through-hole permitting ambient air pressure on the side opposite to the pressure receiving hole in the needle. The pressure sensor is disposed on the support member and is provided with a diaphragm with strain gauges. The diaphragm is located between the through hole and the support member and the pressure receiving hole in the needle. A protective filler material having resiliently elastic and insulating characteristics covers the surface of the pressure sensitive diaphragm and faces the side hole.

U.S. Pat. No. 4,722,348 shows a semiconductor mounted within a tubular housing in the end of the catheter tube and having a pressure inlet. Sealant protects the semiconductor which is held to the support by the double face adhesive tape which also carries the electrical conductors. U.S. Pat. No. 4,809,704 discloses catheters with the sensor mounted in the tip of the catheter supported on a base by a potting resin carried within the catheter tube. The resin is a urethane or silicone material about the sensor with appropriate openings for sampling. Assembly of the sensors within the catheters has been slow and labor intensive.

SUMMARY OF THE INVENTION

The preferred catheter sensor assembly and support includes a member with a distal end and a proximal extension joined by an intermediate part. A passage opens in a first direction and extends along the proximal extension and across the intermediate part; a sensor is carried upon and overlies the passage intermediate part near the distal end. As used herein the term catheter may include a probe which carries the sensor and the connections thereto. The sensor has a bottom and a top so that when the top faces in the first direction the sensor covers the passage with its bottom in communication with a distal portion of the passage and the proximal extension. Conductors attach to an area of the sensor bottom for transmitting signals from the sensor through the lumen. An adhesive sealant between the sensor and the intermediate part about the bottom secures the sensor to the intermediate part near the distal end with the sealant also across the conductors so that the passage remains open between the lumen and the bottom.

The preferred embodiment of the member may be elongate with the distal end shaped to ease insertion of the catheter sensor assembly into a patient and the proximal extension shaped for fitment of the member into the lumen of the catheter tube. The member between the distal end and the intermediate part might have an abutment for longitudinally locating the sensor. The member could include a shoulder between the intermediate part and the proximal extension to abut in face to face relation with the distal end of the catheter tube forming a uniform tubular combination of catheter tube and member which terminates distally at the distal end of the member.

The preferred member may have a lower section with a curved bottom defining the tubular shape of the elongate member so that when the proximal extension is fit within the lumen the tubular member extends distally therefrom. In a particular embodiment the distal end of the member has a diameter approximately that of the catheter tube and the lower section has a radius of curvature approximately that of the catheter tube.

The preferred sensor is a semiconductor chip sealed to the intermediate part and responsive to the pressure differential between the pressure on its planar bottom surface and on an inside base of a recess thereabove. The passage may be relatively narrow and elongate within the proximal extension and enlarged longitudinally and laterally within the intermediate part. The enlarged part of the passage can have a rim with an end and two sides which carry the sensor bottom planar surface about a portion thereof.

The area of the sensor bottom planar surface is preferably near the proximal extension for transmitting signals from the sensor through the lumen. A tube may be positioned in the passage to extend from the lumen to the bottom of the sensor. The proximal extension is sealed with an additional sealant deposit across the conductors and a distal end of the lumen forming a substantially fluid tight connection over the conductors. The tube provides a passageway between the sensor bottom and the lumen in the preferred embodiment.

The sensor in the preferred embodiment has a Wheatstone bridge circuit to provide a signal that varies with load applied to the inside base of the recess. Four sites for electrical attachment of the conductors to the Wheatstone bridge circuit are provided on the bottom planar surface of the sensor chip near the area thereof adjacent the proximal extension. The conductors extend from the sites into and through the passage in the proximal extension and into the lumen which is in fluid communication with the passage.

The member is substantially rigid and the catheter tube is substantially flexible. The member could be made of many materials but it is preferred that metal be used. The catheter tube is most preferably extruded from a polymer such as polyurethane although other polymers can perform as well. The catheter tube could alternately have multiple lumens with a first lumen for connection with the tube, passage and the bottom of the sensor and a second lumen is in fluid communication with the top of the sensor so the lumens each have distal ends in communication with opposite sides of the sensor. The member and catheter tube are size and cross sectionally compatable forming a uniform tubular combination which terminates distally at the distal end of the member.

A method for assembling and supporting a sensor at a distal end of a catheter tube is also a part of the preferred invention. The method comprises several steps including attaching a sensor with an area toward an end thereof for connection to electrical conductors for transmitting input to and signals from a distal end of a catheter tube. Then the step of mounting the sensor to a member with a distal end to ease insertion of the catheter tube into a patient and a proximal extension shaped for fitment of the support into a lumen of the catheter tube, the catheter distal end and the proximal extension joined by an intermediate part for carrying the sensor upon and partially above with the area near the proximal end. The further step of inserting the proximal extension into the lumen with the electrical conductors passing through the lumen.

Thereafter the step of sealing the sensor to a passage open in a first direction and the passage extending along the proximal extension and across the intermediate part by securing the sensor to the member on the intermediate part near the distal end and in the area with sealant while leaving a part of the passage free of sealant so that the sensor is in fluid tight and electrical communication with the passage. The method may also have the step of inserting the proximal extension within the lumen preceded by a step of passing the electrical conductors through the lumen. The step of attaching the sensor to electrical conductors for transmitting input to and signals from a distal end of a catheter tube may be preceded by a step of passing the electrical conductors through the lumen.

The step of sealing the sensor might be followed by a step of sealing with an additional sealant deposit in a distal end of the lumen and across the sensor near the proximal extension to form a fluid tight connection and to leave the passage beneath the sensor in fluid and electrical communication with the lumen. The step of sealing the sensor may alternately be preceded with the step of placing a tube in the passage to provide a passageway between the distal end of the lumen and the sensor.

The invention may be merely a support comprising a member with a distal end and a proximal extension shaped for fitment of the support into a lumen of a tube wherein the distal end and the proximal extension are joined by an intermediate part. A lower section of the member extends from the distal end to the proximal extension. A curved bottom defining the tubular shape of the elongate member may be included on the section so when the proximal extension is fit within the lumen the tubular member extends distally therefrom. A passage extending along the proximal extension and across the intermediate part is relatively narrow and elongate within the proximal extension and is enlarged laterally within the intermediate part. A shoulder may be provided on the member between the intermediate part and the proximal extension to abut in face to face relation with the distal end of a catheter tube forming a uniform tubular combination of the catheter tube and the member. A rim preferably with an end and two sides about the enlarged part of the passage carries the sensor about a portion thereof leaving another part unsupported by the rim.

BRIEF DESCRIPTION OF THE DRAWINGS

FIG. 2 is a partial exploded perspective view of the assembly of FIG. 1 showing the member and the sensor.

FIG. 3 is a side sectional view taken along line 3—3 of FIG. 2 showing the sensor mounted in the end cap and the end cap inserted into the end of a catheter tube with sealant holding the sensor to the end cap and the catheter tube.

DETAILED DESCRIPTION

Figure 1:
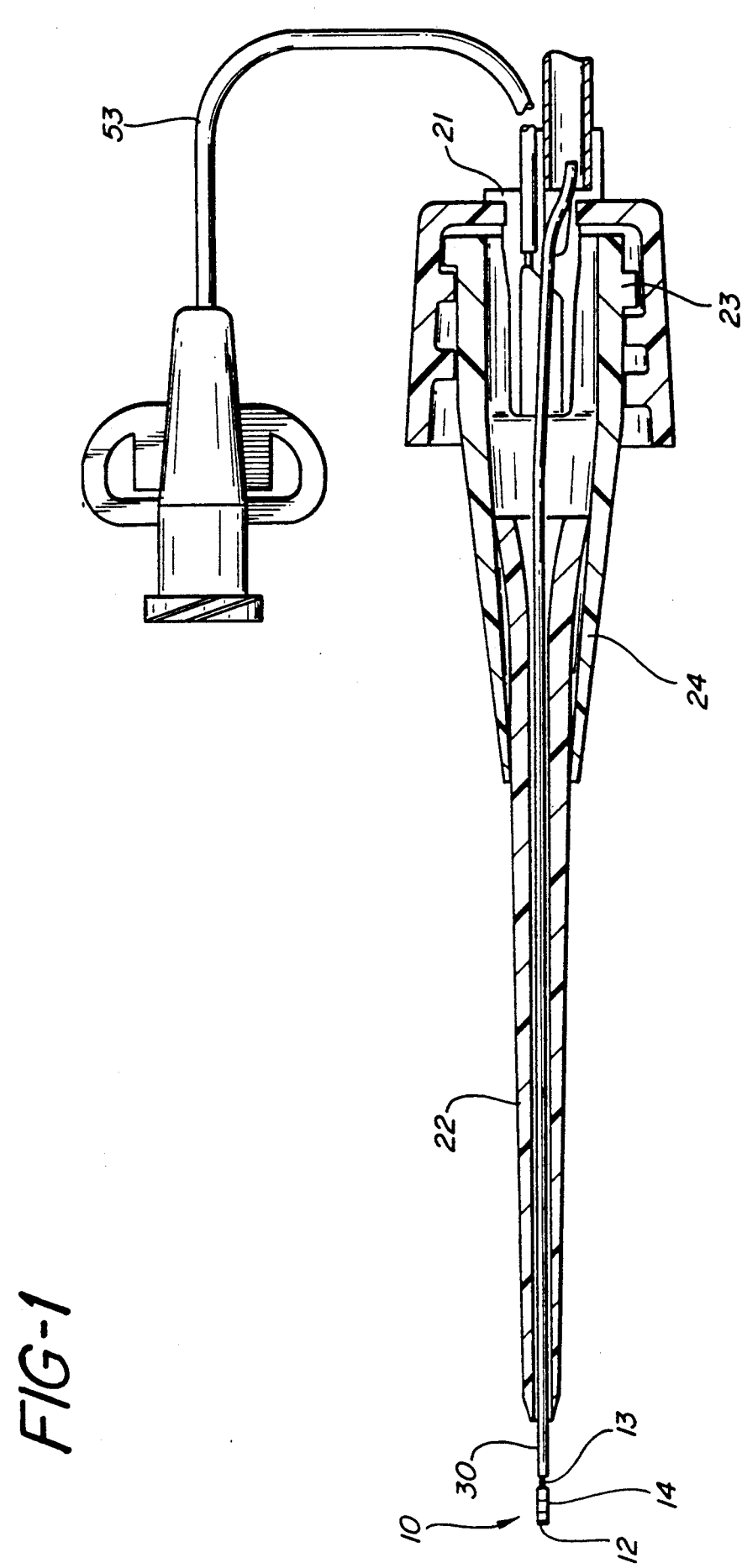
FIG. 1 is an overall plan view of the preferred assembly of the catheter tip pressure sensor as it is attached to a connector for taking blood samples and to a lumen to conveying the electrical conductors to a monitor.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

The preferred catheter sensor assembly and support 10 shown in FIGS. 1, 2 and 3 includes a member 11 with a distal end 12 and a proximal extension 13 joined by an intermediate part 14. The member 11 is preferably cast of medical grade 300 stainless steel or a zirconium loaded alumina ceramic. A passage 15 in the member 11 opens in a first direction, shown as upwardly by an arrow in FIGS. 2 and 3 and extends along the proximal extension 13 and across the intermediate part 14. A sensor 16, illustrated as separate from the member 11 in the exploded view in FIG. 2, is carried upon and overlies the passage 15 in the intermediate part 14 near the distal end 12. The sensor 16 has a bottom 17 and a top 18 so that when the top 18 faces upwardly or in the first direction the sensor 16 covers the passage 15 with its bottom 17 in communication with a distal portion 19 of the passage 15 and a catheter lumen 20.

FIG. 1 is an overall plan view of the catheter sensor assembly and support 10 shown connected to a connector 21 which is described and claimed in a patent application, U.S. Ser. No. 246,476; that application is incorporated herein by reference. The connector 21, shown in cross section, cooperates by luer attachment with an insertion catheter 22, also in cross section, to permit sampling or infusion of medication into the patient. More specifically, the insertion catheter 22 is placed in the patient in an over the needle procedure and the needle (not shown) is withdrawn and removed. The catheter sensor assembly and support 10 is inserted distal end 12 first into the placed insertion catheter 22 and the connector 21 is attached to a luer fitting 23 on an adapter 24 on the insertion catheter 22. Conductors 25 (FIGS. 2 and 3) from the sensor 16 (FIGS. 2 and 3) pass through the connector 21 and are separated from the fluid flowing between insertion catheter 22 and the catheter sensor assembly and support 10 carried therein, as shown in FIG. 1.

The conductors 25 attach to an area 26 of the sensor 16 bottom 17 for transmitting signals from the sensor 16 through the lumen 20; this is shown in cross section in FIG. 3. An adhesive sealant 27 secures the sensor 16 and the intermediate part 14 near the distal end 12 with the sealant 27 also across the conductors 25 so that the passage 15 remains open between the lumen 20 and the bottom 17. The adhesive sealant 27 is applied by dipping the member 11 in a relatively thin liquid form of the adhesive sealant 27 before attaching the sensor 16. An additional sealant 28 may be applied over the sensor 16 to seal the sensor 16 to the member 11 across edges 29 thereof. The preferred adhesive sealant 27 and the additional sealant 28 are in the preferred embodiment a silicone compound of low viscosity to facilitate application of the adhesive sealant 27, such as and for example, by dipping the member 11 assembled into the lumen 20 of a catheter tube 30.

The preferred embodiment of the member 11 may be elongate having a length B along axis A that is approximately six to seven times its width C. The distal end 12 is shaped with rounded corners 31 to ease insertion of the catheter sensor assembly and support 10 into a patient and the proximal extension 13 is shaped with a curved cross section 32 for fitment of the member 11 into the lumen 20 of the catheter tube 30. The member 11 between the distal end 12 and the intermediate part 14 includes an abutment 33 for longitudinally locating the sensor 16 thereagainst to position the sensor 16 lengthwise along the axis A of the member 11. The member 11 has a shoulder 34 located between the intermediate part 14 and the proximal extension which extends radially to abut in face to face relation with a distal end 35 of the catheter tube 30, see FIG. 3. The abutting relation forms a uniform diameter for catheter tube 30 and member 11 with a uniform diameter of about 0.6 mm which terminates at the distal end 12 of the member 11.

A lower section 36 on the member 11 with a curved bottom 37 defines the tubular shape of the elongate member 11 so that when the proximal extension 13 is fitted within the lumen 20, the tubular member 11 extends distally therefrom, as explained, continuing the tubular shape thereof. In a particularly preferred embodiment, the distal end 12 of the member 11 has its diameter approximately that of the catheter tube 30 and the lower section 36 has a radius of curvature about 0.3, mm approximately that of the catheter tube 30. The diameter can be larger or smaller but the preferred diameter for the catheter sensor assembly and support 10 is about 0.6 mm.

The preferred sensor 16 is a semiconductor chip sealed to the intermediate part 14 and responsive to the pressure differential between atmospheric pressure on its planar bottom 17 surface (second side) and its top (first side) 18. The top 18 of sensor 16 preferably has an open recess 38 so that the recess 38 faces in the first direction when the sensor 16 covers the passage 15 with the bottom 17 planar surface in communication with a distal portion 19 of the passage 15 and the lumen 20. The passage 15 may be relatively narrow and elongate within the proximal extension 13 and enlarged longitudinally and laterally within the intermediate part 14. The enlarged part 39 of the passage 15 can have a rim 40 with an end 41 and two sides 42 which carry the sensor 16 bottom 17 planar surface about a portion 43 thereof in FIG. 2.

The area 26 for transmitting signals from the sensor 16 through the lumen 20 is preferably near the sensor 16 bottom 17 planar surface toward the proximal extension 13. It is preferred that a tube 44, positioned in the passage 15, extend from the lumen 20 to the bottom 17 of the sensor 16. The proximal extension 13 at the lumen 20 is sealed with the additional sealant 28 deposited across the conductors 25 and a distal end 45 of the lumen 20 forming a substantially fluid tight connection over the conductors 25. The tube 44 provides a passageway 46 between the sensor 16 bottom 17 and the lumen 20 in the preferred embodiment.

The sensor 16 in the preferred embodiment has a Wheatstone bridge circuit to provide a signal that varies with load applied to an inside base 47 of the recess 38. Four sites 48 for electrical attachment of the conductors 25 to the Wheatstone bridge circuit are provided on the bottom 17 planar surface of the sensor 16 chip near the area 26 thereof adjacent the proximal extension 13. The conductors 25 are bonded as for example by welding to the sites 48 and extend from the sites 48 into and through the passage 15 in the intermediate part 14 and the proximal extension 13 and into the lumen 20 which is in fluid communication with the passage 15.

The member 11 is substantially rigid and the catheter tube 30 is substantially flexible. The member 11 could be made in many ways and of many materials but it is preferred as mentioned that cast metal or a zirconium loaded alumina ceramic can be used. Any relatively rigid material would be acceptable; in particular, ceramic, plastic, glass and the like could be used. The member 11 can machined, molded, stamped, cast or otherwise fashioned. The catheter tube 30 is most preferably extruded from a polymer such as polyurethane although other polymers can be used as well. The catheter tube 30 could alternately have multiple lumens 20 with a first lumen 49 for receiving the tube 46 and the proximal extension 13 and a second lumen 50 shown in FIG. 3 for fluid communication with the top 18 of the sensor 16 so the lumens 49 and 50 each have distal ends 51 and 52 in communication with opposite sides of the sensor 16.

A method for assembling and supporting the sensor 16 at the distal end 35 of the catheter tube 30 is also a part of the preferred invention. The method comprises several steps including attaching the sensor 16 with the area 26 toward the proximal end thereof for connection to electrical conductors 25 for transmitting input to and signals from the distal end 35 of the catheter tube 30. Then performing the step of mounting the sensor 16 to the member 11 with its distal end 12 shaped to ease insertion of the catheter sensor assembly and support 10 into a patient and the proximal extension 13 shaped for fitment into the lumen 20 of the catheter tube 30. The member 11 has the distal end 12 and the proximal extension 13 joined by an intermediate part 14 for carrying the sensor 16 upon and partially above the passage 15 opening in the first direction. The further step is performed of inserting the proximal extension 1 into the lumen 20 with the electrical conductors 25, connected to the proximal end of the bottom 17 of the sensor 16, passing through the lumen 20.

Thereafter the step of sealing is accomplished on the sensor 16 at the passage 15 over the intermediate part 14 by securing the sensor 16 to the member 11 on the intermediate part 14 near the distal end 12 and in the area 26 with sealant 27 while leaving a part of the passage 15 free of sealant 27 so that the sensor 16 is in fluid tight and electrical communication with the passage 15 as shown in FIG. 3. The method may also have the step of inserting the proximal extension 13 preceded by first doing a step of passing the electrical conductors 25 through the lumen 20. Alternately, the step of attaching the sensor 16 to the electrical conductors 25 may be preceded by initially finishing a step of passing the electrical conductors 25 through the lumen 20.

The step of sealing the sensor 16 might be followed by completing a step of sealing with the additional sealant 28 deposited in the distal end 35 of the lumen 20 and across the sensor 16 near the proximal extension 13 to form a fluid tight connection and to leave the passage 15 beneath the sensor 16 in fluid and electrical communication with the lumen 20. The step of sealing the sensor 16 may be preceded by performing the step of placing the tube 44 in the passage 15 to provide the passageway 46 between the lumen 20 and the sensor 16.

The sensor support or member 11 of the catheter sensor assembly and support 10 as shown in FIG. 3 is a part of the invention. The member 11 has its distal end 12 and its proximal extension 13 shaped for fitment of the member 11 into the lumen 20 of the catheter tube 30. The distal end 12 and the proximal extension 13 are joined by the intermediate part 14. The lower section 36 of the member 11 extends from the distal end 12 to the proximal extension 13. The curved bottom 17, defining the tubular shape of the elongate member 11, may be included on the section 36 so when the proximal extension 13 is fit within the lumen 20 the tubular member 11 extends distally therefrom.

The passage 15, extending along the proximal extension 13 and across the intermediate part 14, is relatively narrow and elongate within the proximal extension 13 and is enlarged laterally within the intermediate part 14. The abutment 33, on the member 11 between the distal end 12 and the intermediate part 14, longitudinally locates the sensor 16 thereagainst. The shoulder 34, on the member 11 between the intermediate part 14 and the proximal extension 13, abuts in face to face relation with the distal end 35 of the catheter tube 30 forming a uniform diameter for the catheter tube 30 and the member 11. The rim 40 preferably with the end 41 and two sides 42 about the enlarged part 39 of the passage 15 carries the sensor 16 about the portion 43 thereof leaving another part unsupported by the rim 40.

The catheter assembly and support 10 carries the sensor 16 at the distal end 35 of the catheter tube 30 for insertion through the insertion catheter 22. In use samples of bodily fluids can be taken through adapter 24 connected to a sample extension 53. The catheter assembly and support 10 can be used for pressure measurement in other (non-vascular) parts of the body and the member 11 may be used to support other types of transducers such as for example ph or gas measuring cells.

What is claimed is:

1. A method for assembling and supporting a sensor with a first side and a second side at a distal end of a catheter tube comprising the steps of:
   a) mounting said sensor to a support member with a distal end shaped to ease introduction of a catheter into a living body and a proximal extension sized and shaped for fitment of said extension into a lumen of said catheter, the said support member distal end and said proximal extension joined by an intermediate part for peripherally supporting said sensor over an open recess in said intermediate part;
   b) attaching said sensor to an area whereupon there is a means for connection to electrical conductors, said conductors transmitting input to and signals from said sensor;
   c) inserting said proximal extension into a lumen of said catheter with said conductors passing through said lumen; and d) peripherally sealing said sensor over said open recess, said recess communicatively connected to said lumen of said catheter and open to said second side of said sensor with said first side of said sensor exposed to said living body.

2. The method of claim 1 wherein the step of inserting the proximal extension within the lumen is preceded by a step of passing the electrical conductors proximally through the lumen.

3. The method of claim 1 wherein the step of attaching the sensor is preceded by a step of passing the electrical conductors through the lumen.

4. The method of claim 1 wherein the step of sealing the sensor is followed by a step of sealing with an additional sealant deposit at the distal end of the lumen to form a fluid tight communicatively connected passage between said lumen and said second side of said sensor.

5. The method of claim 4 wherein the step of sealing the sensor is preceded with the step of placing a tube in the passage to provide a fluidly-communicative passageway between the distal end of the lumen and said second side of said sensor.

* * * * *